United States Patent [19]
Bon

[11] 4,029,315
[45] June 14, 1977

[54] DEVICE FOR AUTOMATICALLY EVALUATING THE BALL THROWING EFFICIENCY OF A FOOTBALL PASSER

[76] Inventor: Michel- Julien- Marius- Auguste Bon, 27 avenue Godefroy Cavaignac, 94100 Saint-Maur, France

[22] Filed: June 19, 1975

[21] Appl. No.: 588,317

[30] Foreign Application Priority Data

June 27, 1974 France .............................. 74.22370

[52] U.S. Cl. ...................... 273/55 R; 273/102.2 R; 273/183 R; 273/184 R; 340/323 R
[51] Int. Cl.² .......................................... A63B 67/00
[58] Field of Search .... 273/55 R, 102.2 R, 102.2 S, 273/183 R, 184 R, 185 A, 125 A, 176 F, 176 A, 101.1, 102.2; 250/209, 222 R; 235/92 GA; 340/323 R

[56] References Cited

UNITED STATES PATENTS

| | | |
|---|---|---|
| 2,102,166 | 12/1937 | Roberts ........................ 273/184 R |
| 2,784,001 | 3/1957 | Simjian ......................... 273/185 A |
| 3,160,011 | 12/1964 | Ogden ........................... 273/184 R |
| 3,194,562 | 7/1965 | Speiser .......................... 273/184 R |
| 3,513,707 | 5/1970 | Russell et al. .............. 273/183 R X |
| 3,589,732 | 6/1971 | Russell ....................... 273/185 A X |
| 3,655,202 | 4/1972 | Sanders et al. ................ 273/184 R |
| 3,727,069 | 4/1973 | Crittenden et al. ........ 273/102.2 X |
| 3,769,894 | 11/1973 | Conklin .......................... 273/185 A |

*Primary Examiner*—Harland S. Skogquist
*Assistant Examiner*—T. Brown

[57] ABSTRACT

The device for evaluating the efficiency of a ballplayer is provided with a target generator to control means whereby a visible target is rendered visible in a goal surface; the device further comprises means for measuring a parameter in relation with the speed of a ball going toward the goal surface and means for measuring the distance separating the target from the impact of the ball on the goal surface and computing means for determining the efficiency of the player in relation with the speed and position reached by the ball.

6 Claims, 8 Drawing Figures

DEVICE FOR AUTOMATICALLY EVALUATING THE BALL THROWING EFFICIENCY OF A FOOTBALL PASSER

This present invention relates to a device allowing to automatically evaluate the efficiency of a player hitting or throwing or shooting a ball such as a football, handball player, etc... in view of sending said ball in a goal of determined sizes.

It is in fact of interest in the sporting classes to be able to objectively compute the efficiency of a player in an other way than by a personal appreciation, which is of course subjective. In the present method, in fact it is generally satisfactory, for appreciating the performances of a player, to count the hits in the goal upon a series of trials without having specifically the possibility to appreciate the accuracy of the shoots nor the strength thereof.

The efficiency of a player can be considered a priori as a function of two parameters: the accuracy of the shoot and the speed of the ball at the moment where the same reaches the target, or at least its composante according to a direction at right angle with respect to the surface of the goal, easier to measure.

The devices of this type, which are known, and allowing the appreciation of said parameters are pretty rudimentary and do not give any figured and combined measure showing really the natural dispositions of the player to reach, both with power and accuracy, the target which has been pointed out to him. The accuracy, in general, is appreciated by means of a squaring supported by a wall, against which the player makes the ball to hit the same while trying to reach some determined squares. The power of the kick is measured by means of a dynamometer directly hit.

This present invention has, for its object, a device allowing to make a target to appear in any point of the goal surface to be reached by the player, to measure the accuracy of the shoot considered as the distance separating the target from the intersection of the real trajectory of the ball with the goal surface, to measure the speed or a distance in relation with said speed, said speed being the one with which the ball arrives on this goal surface and at least to compute, according to a formula selected a priori, the efficiency of the player by using the preceding measures of the two main parameters considered: speed and accuracy.

As a first approximation, it is possible to admit that the efficiency E of a player is directly proportional to the speed V with which the ball arrives on the target and proportional to the accuracy, this one being defined by the contrary of the distance D separating the target and the intersection of the trajectory of the ball with the plane of the goal surface. In the following it will be admitted that the efficiency of a player to appreciate is given by a relation of the following form:

$$E = K \cdot V \cdot 1/D \quad (1)$$

or more generally:

$$E = K \cdot f(V) \cdot 1/D \quad (2)$$

wherein V is the speed of the ball according to a direction perpendicular to the goal surface; $f(V)$ a function of the speed, in some case where said speed is not directly measured, and K a constant coefficient, characteristic of the device, and allowing for example to establish a quotation varying from 0 to 20, from 0 to 100 or any other scale of adapted appreciation.

This present invention, for that purpose, mentions the utilization of captors with analogic or numerical outlet, furnishing electrical signals representative of the magnitudes V and D to a computer which, depending on the preceding relation (1) or (2), gives directly the measure of the desired efficiency E.

The device according to this present invention is characterized due to the fact that it comprises a device allowing to automatically evaluate the efficiency of a ball player hitting or throwing a ball in viewing a determined target on a goal surface at distance, wherein it comprises:

a target generator associated to control means to make a luminous target appear in a predetermined area of the goal surface;

means for measuring a parameter having relation with the speed of the ball at the impact with the surface of the goal;

means for measuring the distance separating the target from the ball impact on the surface of the goal;

computing means to translate a given relation between said parameter in relation with the speed and the contrary of said distance, the result of this computation being representative, except for one coefficient, of the efficiency watched.

Such a device is especially advantageous for the training of the players and the appreciation of their specific natural dispositions; besides it gives the possibility to proceed to a classification depending on the objective criteria, measured independently of any error of personal appreciation, but only function of the quality of the measuring means embodied.

It must be understood that the word "ball" must be taken in a large effect, the ball can be a ball of variable size depending on the sport considered (football, handball, waterpolo, etc...) or also a quoit (hockey) or any other element for games that the player tries to throw in the adverse goal surface.

Below it will be more particularly described an example of embodiment of this present invention to the football game, but of course said example is not limitative and this present invention can be applied to other games such handball, hockey, water-pole, etc...

Other characteristics of this present invention are shown in the following detailed description.

Embodiment of this present invention is shown by way of none restrictive example in the accompanying drawing and representing a preferred embodiment of a device according to this present invention.

Figure 1:
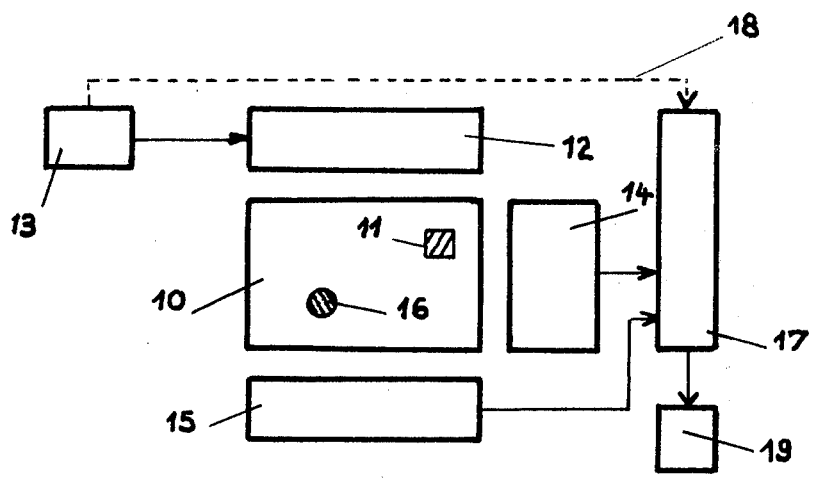
FIG. 1 is a synoptical diagram of a device according to this present invention.

On the diagram shown in FIG. 1, the reference 10 designates the goal surface wherein a target 11 can be shown by a target generator 12 in an area of said surface, determined by means of a target selector 13 controlling said generator. The goal surface 10 is provided with or associated to two series of captors 14 and 15 designed to measure, on one hand the speed V of the ball according to a normal direction of the goal surface, or the kinetic energy $Ec = \frac{1}{2} m V^2$, $m$ designating the ball mass when the same passes through the goal surface; on the other hand, the distance D separating the target II from the place 16 of the goal surface really reached by the ball. The captors 14 and 15 are connected to a computer 17 which, from the data furnished by said captors, makes the product $E = K \cdot V \cdot I/D$ according to the relation (1). In the case where the speed V is not obtained directly from the captors 14 but in the form $Ec = \frac{1}{2} m \cdot V^2$, the computer makes the computation $V = \sqrt{2Ec/m}$, the value of the mass $m$ of the ball being introduced preferably into the computer and being a constante well known.

Also is designed a connection 18 shown in dotted lines between the target selector 13 and the computer 17 thus the area 16 is injected in the computer 17 by the data received by the captors in the form of coordinates $x, y$. The computer 17 then indicates the distance D from the coordinates Xo, Yo of the target 16 furnished by the selector 13. From the data from the captors, the coordinates $x$ and $y$ of the point 16 are given by a simple formula of analytic geometry.

Then, the computer 17 is connected to a posting and recording device where appear in numerical form the values of V, D and E.

The principle of the device being explained, now will be described a practical way of realization of the same and also various types of captors which could be adapted to said device to obtain a measure of the magnitudes V and D.

FIGS. 3, 4, 5, 7 and 8 show a practical way of realizing the structure of a device according to this present invention, applied to a football goal. On the transverse sectional view represented on FIG. 3, it is shown that said device comprises mainly:

on one hand a frame 20, with a rigid metallic frame, strongly fixed in the ground by means of anchorages 21. Said frame delimits the usual goal surface A, B, C, D, by means of two vertical posts of the transverse bar and possibly a second bar 27 used as support at the level of the ground;

on the other hand, placed behind said fixed frame 20, a mobile support 22, with a frame preferably metallic to be practically indeformable, having at least the same surface as the fixed frame 20. Said support is provided with a non-stretching net 23 and with a target generator. The net 23 is placed at the front portion, which means on the side of frame 20 and it is designed to receive and stop the ball and also to transmit to the support the stress received. The target generator whose nature will be ulteriorly indicated, is placed at the rear portion and at a sufficient distance for not being damaged by the ball upon the net motions under the ball impact.

Support 22 is connected to frame 20 by means of four bolts 26 placed in angularly located tubular elements, and it bears on a transverse angle 27 fixed to frame 20. Said support is thus able to move in translation according to a direction perpendicular to the goal surface when the ball, hitting the net 23, communicates to said support its cinetic energy.

The bolts 26 comprise, in the considered example, extensometrical gauges 28 used as dynamometrical captors and whose measures will be utilized both for the computation of the speed V and of the distance D to consider.

FIGS. 3, 4, 5 and 7 show, with more details, a way of realization of the support 22 for placing the net 23 and the target generator.

Support 22 is constituted of four U-shaped irons, marked, assembled by inside angle-irons 36 and outside angle-irons 38 having a cylindrical portion 35 wherein passes the connecting bolt 26 with the frame 20. On each of the four cylindrical portions 35 is welded a fixed pulley 38 used to guide the steel cable 39 which surrounds the support 22 and to which a stretcher 40 allows to give an appropriated tightness. It is on said cable 39 that net 23 is fixed by passing through holes 41 through support 22. On the horizontal portions of the support 22 are bolted vertical U-irons 42 regularly distributed and designed for placing the target generator. Said generator is composed of a set of lamps such as in 43. A lamp 43 is supported by a part 44 fixed on two adjacent irons 42 and through damping devices 45 made of flexible material, rubber or plastic material and on which is placed the tight socket 46 of lamp 43. The bulbs 43 are connected to target selector which allows to light up, as desired, any bulb.

Figure 2:
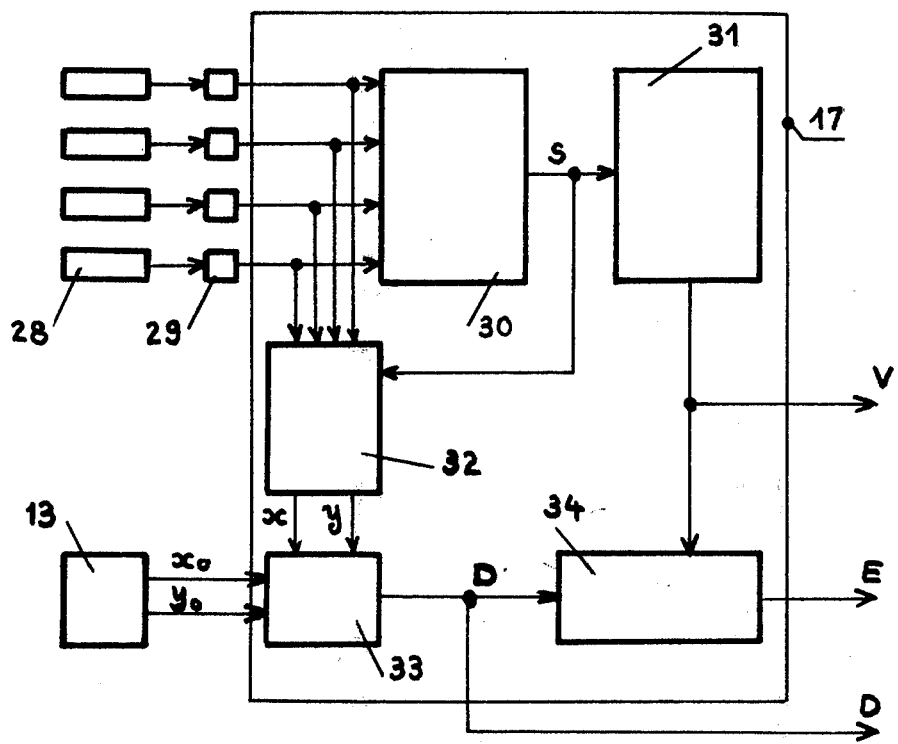
FIG. 2 is the diagram of a computer designed for the embodiment of this present invention.
Figure 3:
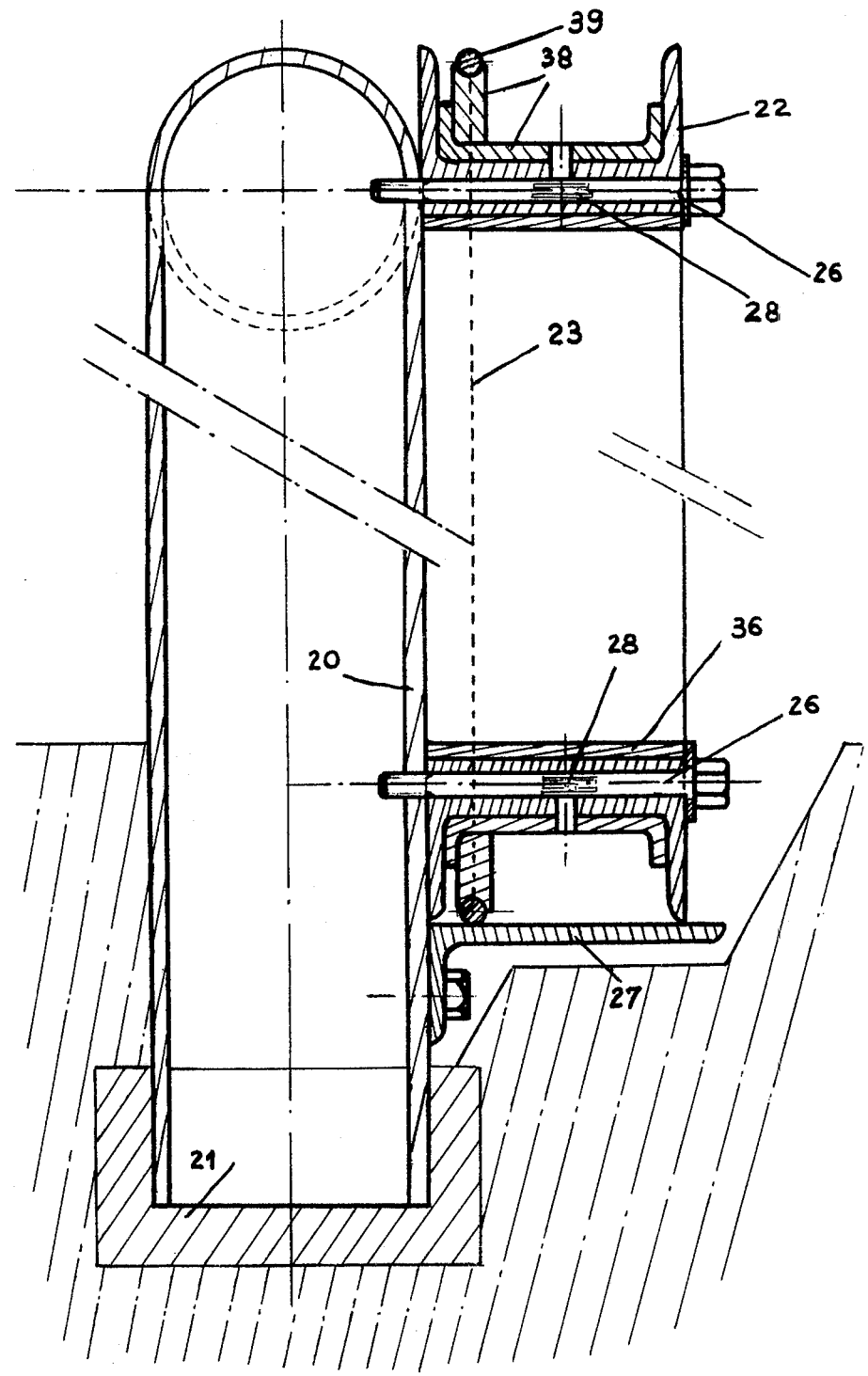
FIG. 3 is a transverse sectional view of the structure of a device realized according to this present invention and applied to a football goal.
Figures 4, 5:
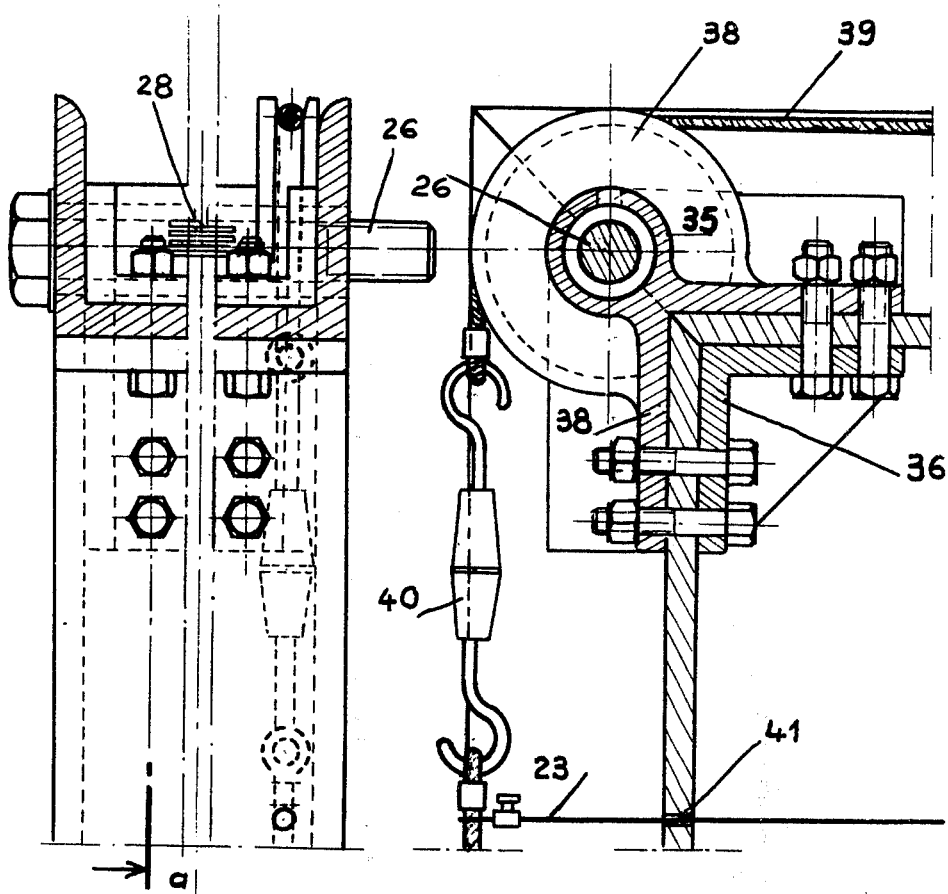
FIG. 4 is a transverse view of a portion of a support of the structure in FIG. 3.
FIG. 5 is a sectional view according to the median plane a in FIG. 4.

With reference now to FIG. 2, will be described the diagram of the computer 17 to which are connected the gauges 28 for the purpose of the treatment of their data and the obtention of values V, D and E previously mentioned. Said computer comprises a circuit 30 making the summation of the output signals appearing from captors after their integration into integrators 29. In fact, as the gauges, because of the resiliency of the support 22, are not instantly operated but with some delay due to the inertia, it is necessary to integrate the signal in view of measuring with accuracy the energy transmitted. The circuit 30 thus furnished a signal proportional to the cinetic energy $Ec = \frac{1}{2} m V^2$. An operational circuit 31 then makes the sum $$V = \frac{\sqrt{2 E_c}}{m},$$

the mass $m$ of the ball being considered as a constant and well-known coefficient.

The computer 17 further comprises another operational circuit 32 used to determine the coordinates $x$ and $y$ of the impact point of the ball signals produced by integrators 29 applied to the same and from signal AS already elaborated by circuit 30. In fact, the changes in stress registered from the gauges are inversely proportional to the distance comprised between the impact point and the measuring point.

Figure 6:
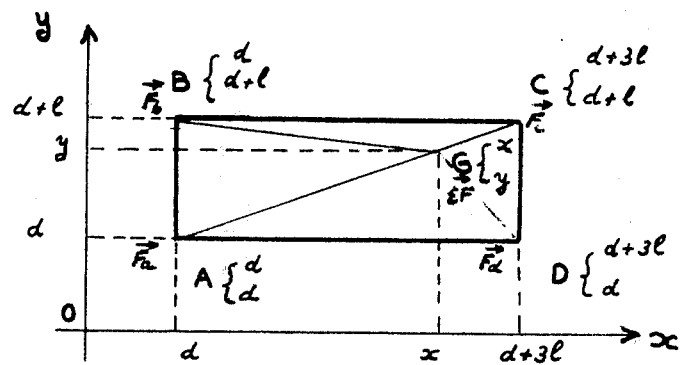
FIG. 6 is an explicative diagram to determine the coordinates of the impact point.
Figure 7:
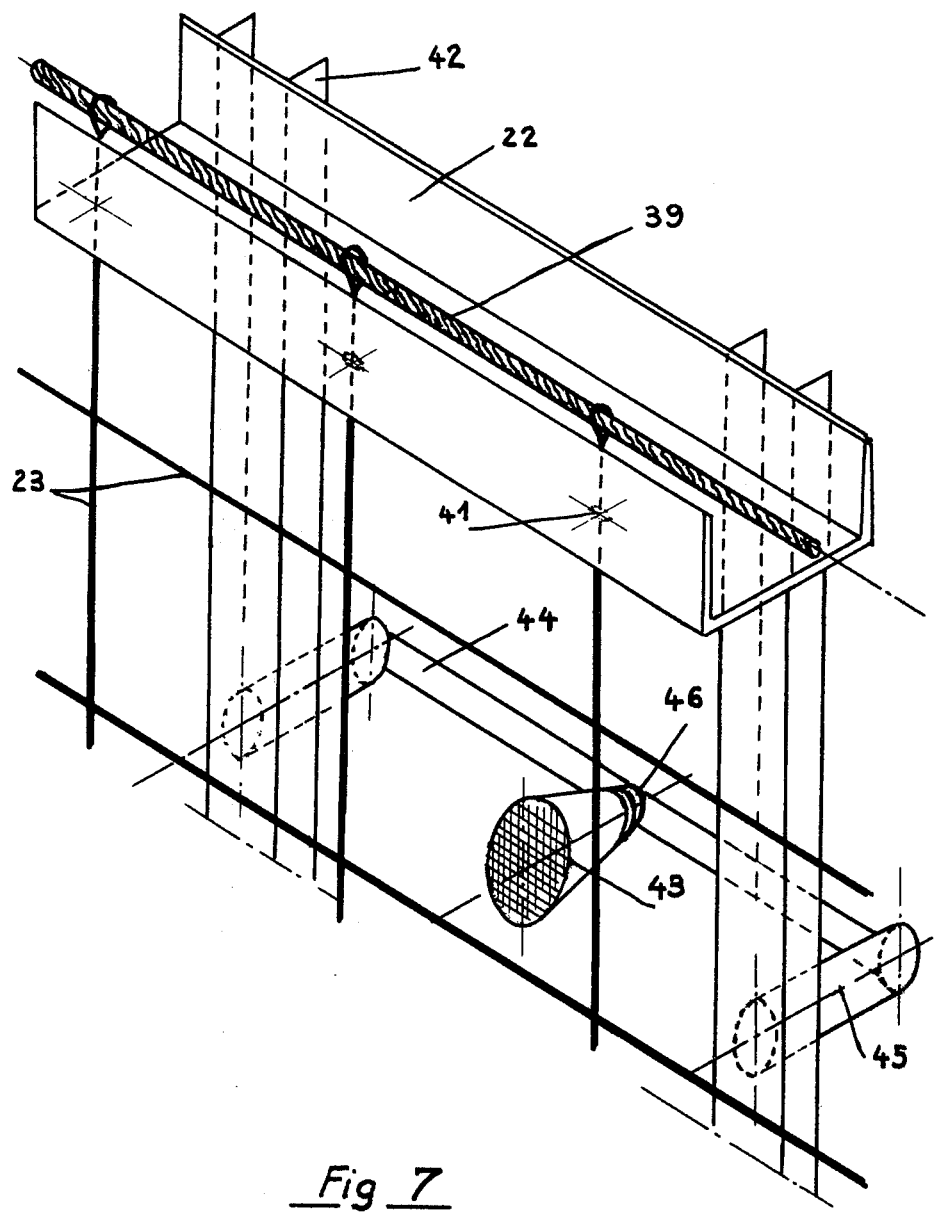
FIG. 7 is a partial perspective view of the support of the preceding figures and diagrammatically showing the placing of a target on said support.

With reference now to FIG. 6, it is noticed that if G designates the impact point of the ball on the goal surface A, B, C, D, Fa, Fb, Fc, Fd, the composantes at points A, B, C and D of the F strength exerted in G and measured by gauges 28 and proportional to the signals coming out from integrators 29, the circuit 32 determines the coordinates $x$ and $y$ of the G point, in relation with a system of rectangular axis $\vec{Ox}$, $\vec{Oy}$, selected parallel to sides A, B, C and D of the rectangle.

Considering the point A $(d, d,)$ with: $l$, the width of the rectangle A, B, C and D and $3l$ the length, are obtained the following coordinates:

B $(d, d + l)$, C $(d + 3l, d + l)$ and D $(d + 3l, d)$.

As $Fa + Fb + Fc + Fd = F$ at point G, G can be considered as the gravity center of the rectangle A, B, C, D.

In writing the moments of Fa, Fb, Fc, Fd, in relation with axis Ox and Oy, is obtained the following relation:

$$Fx = d(Fa + Fb) + (d + 3l)(Fc + Fd) \text{ that is, doing } d = 0$$
$$x = \frac{3l(Fc + Fd)}{Fa + Fb + Fc + Fd}$$

also is obtained the value of:

$$y = \frac{l(Fb + Fc)}{Fa + Fb + Fc + Fd}$$

The length $l$ being known and registered, the circuit 32 performs the computation of $x$ and $y$ in function of the signals received from the gauges 28 and integrator 29 which represent the composantes Fa, Fb, Fc, Fd for example by means of operational amplifiers. The circuit 30 furnishes the signals $S = Fa + Fb + Fc + Fd$.

The computer comprises a third operational circuit 33 which performs the computation of the distance D between the point of coordinates Xo, Yo determined by the target selector (13, FIG. 1) and the point of coordinates $x$ and $y$ determined by circuit 32 by using well-known formula.

A fourth operational circuit 34 connected to the outputs of circuits 31 and 33 perform the final computation of the efficiency: $E = K.V.l/D$.

The outputs of circuits 31, 33, 34 are connected to means of analogic-numerical conversion associated to posting means for visualizing with temporary memory and the recording of numerical results of the measures V, D and E; device 19 (FIG. 1).

This device operates in the following manner: previously, the pre-stress of the four bolts is balanced with the heads of said bolts, their rotation conditioning the tightening of support 22 on frame 20 by an appropriate commutation; the bridge-placing of the gauges allows to perform said balancing with accuracy. The operator having selected a target with the help of the selector 13, said target having coordinates Xo, Yo, the player shoots towards the goal. Considering the ball hits the goal surface, from the signals received from gauges 28, the computer allows the posting of the value of speed V, of distance D and of efficiency E in relation with the shoot considered. After cancelling of temporary memories of visualization, a new shoot can be made on the same target or on a new one determined by means of the selector. The recording of the series of results obtained by one or several players allows, after checking, to establish averages, competitions, etc...

Figure 8:
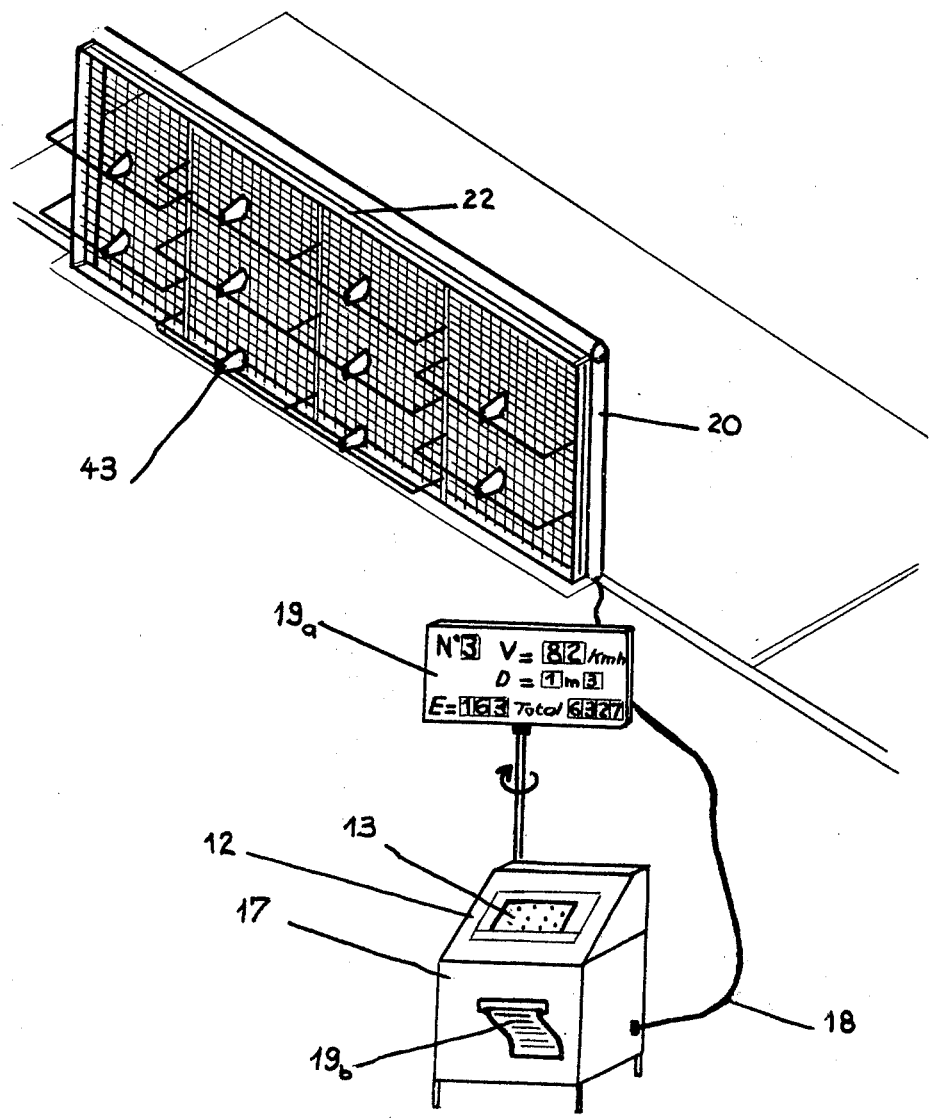
FIG. 8 is a diagrammatic perspective view of a realization of this present invention applied to the football.

FIG. 8 represents a view of a device utilized on a football ground; the goal surface being seen from the back side, is also seen the set of lamps controlled by selector 13.

The data issued from gauges are transmitted by cable 18 to the computer 17 whose computation are shown by the movable indicator 19a and registered by the printer 19b.

Instead of using a selector connected to the computer by wire, it is possible to use a selector which telecontrols the target generator by hertzian or supersonic signals. Also can be considered a self-operation by a programmer which makes target appear in a predetermined sequence and at a variable rate.

In the above described realization, the dynamometric captors can be replaced by captors of another type than extensometric, for example piezo-electrical captors, captors with reluctance variation, capacitive, magnetic, etc... the operational circuits connected downstream being, every time, adapted to the magnitude really measured by said captors (power, quantity of motion, etc...) to furnish in the end the speed and accuracy data desired.

Though this present invention has been described in relation with a special way of realization, given as example, it is well understood that the means embodied to be used as captors of speed and accuracy parameters can be replaced by equivalent means furnishing said same magnitudes, without departing from the scope of this present invention.

With regard to the speed, instead of being deduced from the cinetic energy, it can also be directly measured, for example by means of two electromagnetic barriers, with UHF waves, infrared or visible. Said two barriers placed in parallel with the goal line, the first one then controls the unblocking of a door circuit allowing the transmission of the clock signal of a generator towards a pulse meter, while the second one, close to the goal-line controls the re-blocking of the door circuit. The content of the meter thus measures the time $t$ that the ball has taken to pass the distance $d$ which separates the two barriers; the speed then will be $V = d/t$. The barriers can also be replaced by microphones sensitive to the noises caused when the ball is shooted and when the ball is hitting the net.

Also, the target generator can be independent and separated from the structure of the goals and be constituted by all means allowing to make appear a luminous spot in a selected point and perfectly determined on the goal surface: lamps dies, luminescent lozenges, mobile projector or orientable projector associated to a translucent screen, light source fixed at the end of a rod controlled in abscisses and in ordinates by telescopic means or step to step motors, etc... The only condition to comply with is that coordonates of spot Xo, Yo in relation with the goal surface can be transmitted to the operational circuit (33, FIG. 2) for the computation of distance D. The operational circuits, such as circuits 31 to 34 can be realized with a basic of operational amplifiers performing in a well-known way the simple arithmetical operations, or with a base of circuits for numerical computations preceded by analogical-numerical converters of the anlogical input data. The circuit, extracting square roots, can be of any type known, with no difference with respect to this present invention.

I claim:

1. A ball game practice and computing system in which a ball is thrown by a player from a normal rest position towards a goal surface and reaches the goal surface with an instantaneous speed, said system comprising:

a target generator for providing a visible target on the goal surface;

means to control said target generator, whereby the visible target appears in a selected area of the goal surface;

means for measuring the distance between the visible target and a point on the goal surface which is impacted by the ball thrown by the player;

means for measuring a parameter related with the instantaneous speed of the ball at said impact point;

means connected to the two said measuring means for computing a given relation between the parameter related to said speed and said distance, whereby the ratio of said parameter and of said distance is a data characterizing efficiency of the player.

2. The system as set forth in claim 1, wherein the ball has a kinetic energy at the impact with the goal surface, and said speed measuring means comprises dynamometric probes operatively connected to the goal surface and sensitive to impact of the ball on the goal surface, said probes being connected to integrating and summing circuits to provide an output signal characteristic of the kinetic energy of the ball at the impact surface.

3. The system as set forth in claim 2, further comprising a further operational circuit to the integrating and summing circuits to convert said output signal into signals representative of the speed of the ball at the impact surface.

4. The system as set forth in claim 1, wherein said distance measuring means comprises:

dynamometric probes sensitive to impact of the ball on the goal surface;

a first operational circuit connected to said probes for converting signals from said probes into signals representing the coordinates of the impact point in a reference system;

a second operational circuit connected to the target generator control means to determine coordinates of the target in the reference system;

a third operational circuit connected to said first and second operational circuits to determine the distance separating the impact point from the target.

5. The system as set forth in claim 4, further comprising:

a rigid and fixed frame delimiting the goal surface; and a net placed on a support mobile with respect to said frame to stop the ball and transmit to said support an impact force, said dynamometric probes being connected to said support to give signals representative of local components of the impact force of the ball on the net.

6. The system as set forth in claim 5, further comprising securing elements connecting said mobile support to the fixed frame, and wherein said dynamometrical probes comprise extensometric gauges mounted on said securing elements.

* * * * *